(12) United States Patent
Hirose et al.

(10) Patent No.: US 8,153,822 B2
(45) Date of Patent: Apr. 10, 2012

(54) FLUORENE COMPOUND

(75) Inventors: Hidekazu Hirose, Kanagawa (JP); Koji Horiba, Kanagawa (JP); Akira Imai, Kanagawa (JP); Takeshi Agata, Kanagawa (JP); Katsuhiro Sato, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 295 days.

(21) Appl. No.: 12/552,699

(22) Filed: Sep. 2, 2009

(65) Prior Publication Data
US 2010/0197942 A1 Aug. 5, 2010

(30) Foreign Application Priority Data
Feb. 2, 2009 (JP) ................. 2009-021538

(51) Int. Cl.
*C07D 409/04* (2006.01)
*C07D 409/14* (2006.01)

(52) U.S. Cl. ....................................... 549/59
(58) Field of Classification Search ............ 549/59
See application file for complete search history.

(56) References Cited

FOREIGN PATENT DOCUMENTS
JP A-11-273863 10/1999
JP A-2003-55275 2/2003
JP A-2007-126403 5/2007

OTHER PUBLICATIONS

Contoret et al., Chem Materials (2002), vol. 14(4), pp. 1477-1487.*
Aldred et al, J. Materials Chem. (2005), vol. 15(31), pp. 3208-3213.*
Aldred et al, Liq. Crystals, (2008) vol. 35(4), pp. 413-427.*
Liedtke et al, Chem. Materials, (2008) vol. 20(11), pp. 3579-3586.*
Woon et al, Chem. Materials, (2006) vol. 18(9), pp. 2311-2317.*
Aldred et al, Adv. Materials, (2006) vol. 18(13), pp. 1754-1758.*
Sato et al., "Application of Organic EL Device to Flat Panel Display," Technical Report of IEICE, The Institute of Electronics, Information and Communication Engineers, OME 95-54, 1995, pp. 47-52.
Waxamoto et al,, "Organic Electroluminescence Devices with a Starburst Amine as a Hole Transport Material," The 40th Meeting, Japan Society of Applied Physics & Related Societies, 30a-SZK-14, 1993, p. 1146.

* cited by examiner

*Primary Examiner* — Taofiq A Solola
(74) *Attorney, Agent, or Firm* — Oliff & Berridge, PLC

(57) ABSTRACT

A fluorene compound is provided, which is represented by the following Formula (I):

Formula (I)

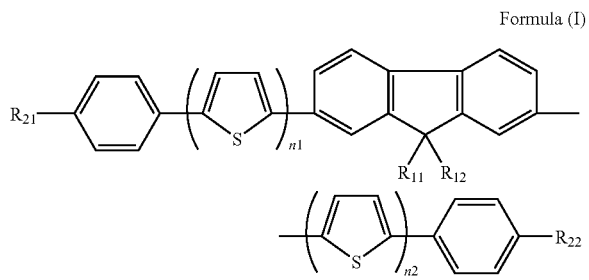

in Formula (1), $R_{11}$ and $R_{12}$ each independently represent an alkyl group having 1 to 6 carbon atoms; $R_{21}$ and $R_{22}$ each independently represent an alkyl group having 1 to 8 carbon atoms, or an alkoxy group having 1 to 8 carbon atoms; and n1 and n2 each independently represent an integer of from 1 to 5.

20 Claims, 2 Drawing Sheets

INFRARED ABSORPTION SPECTRUM OF COMPOUND OBTAINED IN EXAMPLE 2

NMR SPECTRUM OF COMPOUND OBTAINED IN EXAMPLE 2

FLUORENE COMPOUND

CROSS-REFERENCE TO RELATED APPLICATION

This application claims priority under 35 USC 119 from Japanese Patent Application No. 2009-021538 filed on Feb. 2, 2009.

BACKGROUND

1. Technical Field

The present invention relates to a novel fluorene compound.

2. Related Art

As charge transport materials for organic electronic devices, charge transport polymers represented by polyvinylcarbazole (PVK), diamino compounds such as N,N'-di(m-tolyl)-N,N'-diphenyl benzidine and 1,1-bis[N,N-di(p-tolyl)aminophenyl]cyclohexane, and low molecular compounds of 4-(N,N-diphenyl)aminobenzaldehyde-N,N-diphenylhydrazone are well known. For organic electrophotographic photoreceptors currently used in copying machines or printers, dispersions, in which low molecular compounds are dispersed in a polymer, are mainly used, because it enables high functionalization of the photoreceptors owing to a variety of materials, combinations of low molecular compounds and polymers, and the like. Further, charge transport polymers are also studied as photoconductive materials and charge transport materials for electrophotographic photoreceptors from the viewpoint of high functionalization and long life.

In recent years, with the development of highly functionalized organic electrophotographic photoreceptors, electrophotographic photoreceptors have also come to be used for high-speed copying machines and printers. In the electrophotographic photoreceptors, it is required to use charge transport materials having a high charge transport capability in addition to materials with high charge generating efficiency. This is because charges generated in a charge generating material by light irradiation under the application of an electric field are efficiently received by the charge transport materials and are rapidly transported into a photoreceptor layer. A charge transport material, which has higher charge transport capability and efficiently receives charges generated in a charge generating material, is desired, and is under intensive research.

Further, in recent years, these charge transport materials are also being used for organic electroluminescent elements.

Furthermore, in recent years, organic devices, in particular, organic electroluminescent elements, in which a fluorene compound is used, have been reported.

SUMMARY

According to an aspect of the invention, there is provided a fluorene compound represented by the following Formula (I):

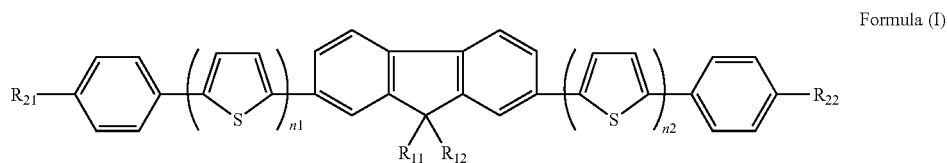

Formula (I)

wherein, in Formula (I), $R_{11}$ and $R_{12}$ each independently represent an alkyl group having 1 to 6 carbon atoms; $R_{21}$ and $R_{22}$ each independently represent an alkyl group having 1 to 8 carbon atoms, or an alkoxy group having 1 to 8 carbon atoms; and n1 and n2 each independently represent an integer of from 1 to 5.

BRIEF DESCRIPTION OF THE DRAWINGS

Exemplary embodiments of the present invention will be described in detail based on the following figures, wherein.

DETAILED DESCRIPTION

Figure 1:
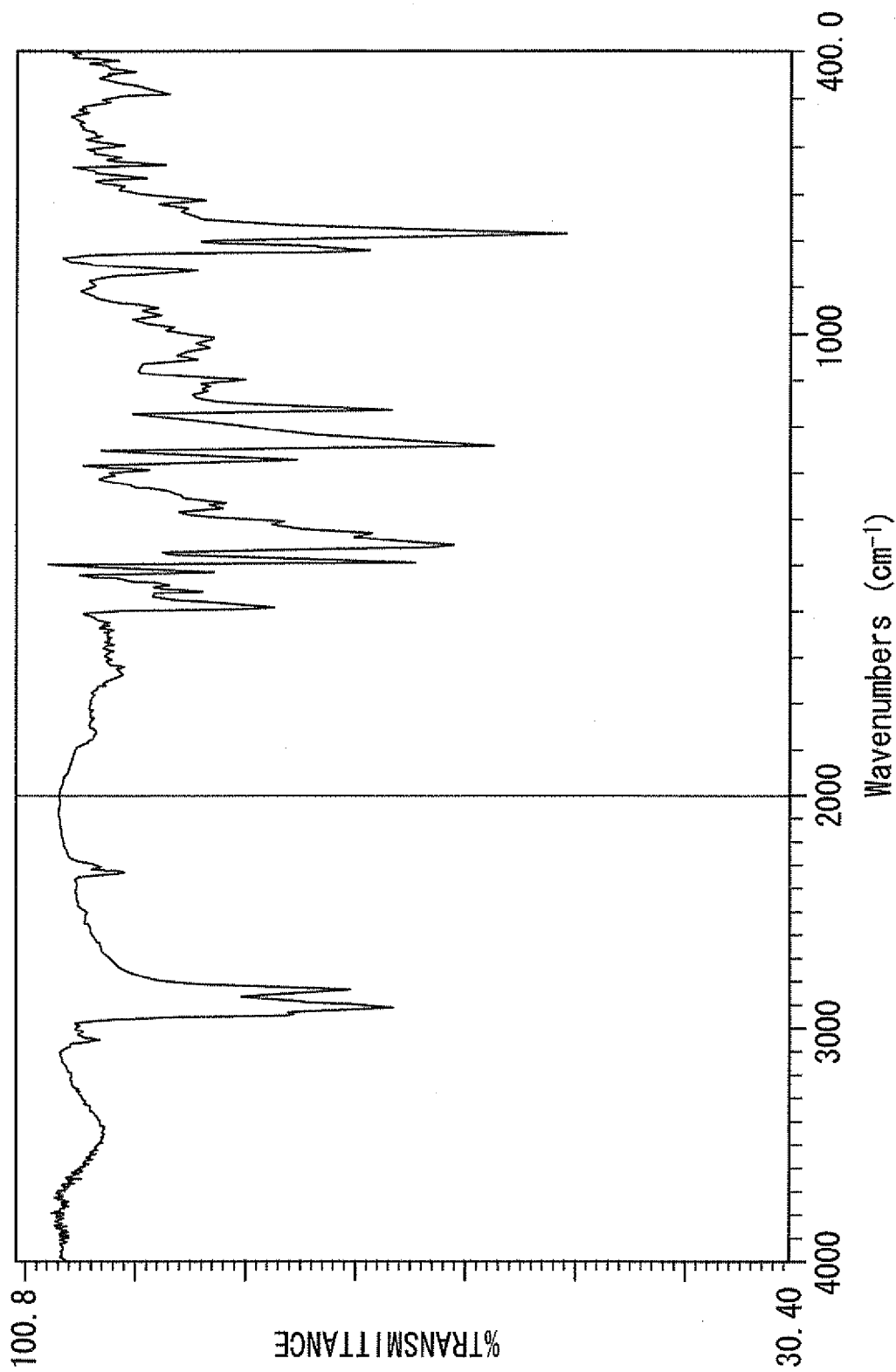
FIG. 1 is a graph showing the infrared absorption spectrum of the compound obtained in Example 2.

According to an aspect of the invention, there is provided a novel fluorene compound having solubility and film-formability, and having charge property (charge transport property and charge injection property).

The fluorene compound according to an exemplary embodiment of the invention is the fluorene compound represented by the following Formula (I):

Formula (I)

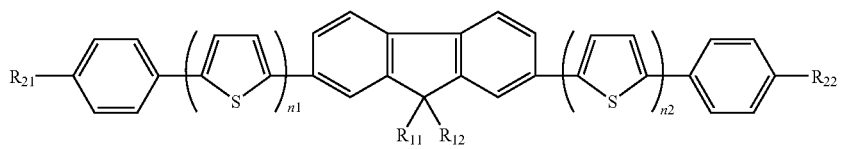

In Formula (I), $R_{11}$ and $R_{12}$ each independently represent an alkyl group having 1 to 6 carbon atoms; $R_{21}$ and $R_{22}$ each independently represent an alkyl group having 1 to 8 carbon atoms, or an alkoxy group having 1 to 8 carbon atoms; and n1 and n2 each independently represent an integer of from 1 to 5.

In Formula (I), the alkyl group represented by $R_{11}$ or $R_{12}$ is an alkyl group having 1 to 6 carbon atoms (preferably, 3 to 6 carbon atoms), and more specifically, the examples thereof include a methyl group, an ethyl group, an n-propyl group, an isopropyl group, an n-butyl group, a t-butyl group, a pentyl group and a hexyl group. The alkyl group represented by $R_{11}$ or $R_{12}$ may be straight-chained or branch-chained.

In Formula (I), the alkyl group represented by $R_{21}$ or $R_{22}$ is an alkyl group having 1 to 8 carbon atoms (preferably, 3 to 6 carbon atoms), and more specifically, the examples thereof include a methyl group, an ethyl group, an n-propyl group, an isopropyl group, an n-butyl group, a t-butyl group, a pentyl group, a hexyl group, a heptyl group and an octyl group. The alkyl group represented by $R_{21}$ or $R_{22}$ may be straight-chained or branch-chained.

In Formula (I), the alkoxy group represented by $R_{21}$ or $R_{22}$ is an alkoxy group having 1 to 8 carbon atoms (preferably, 3 to 6 carbon atoms), and more specifically, the examples thereof include a methoxy group, an ethoxy group, an n-propoxy group, an isopropoxy group, an n-butoxy group, a t-butoxy group and a pentyloxy group. The alkoxy group represented by $R_{21}$ or $R_{22}$ may be straight-chained or branch-chained.

In Formula (I), n1 and n2 each independently represent an integer of from 1 to 5, and preferably an integer of from 1 to 3.

The fluorene compound according to the exemplary embodiment may be a symmetrical compound, or an asymmetrical compound. Namely, according to exemplary embodiments, the fluorene compound may be a symmetrical compound, where $R_{11}$ and $R_{12}$, $R_{21}$ and $R_{22}$, and n1 and n2 are the same, respectively, or may be an asymmetrical compound, where members in at least one of the pairs are different from each other.

Hereinafter, specific examples of the fluorene compound of the exemplary embodiment are shown, but the invention is not limited to these examples. In addition, the numerals in "Structure No" denote the numbers of the exemplary compounds as specific compounds.

| Structure No. | $R_{11}$ | $R_{12}$ | $R_{21}$ | $R_{22}$ | n1 | n2 |
|---|---|---|---|---|---|---|
| 1 | —CH$_3$ | —CH$_3$ | —CH$_3$ | —CH$_3$ | 1 | 1 |
| 2 | —CH$_3$ | —CH$_3$ | —CH$_3$ | —CH$_3$ | 2 | 2 |
| 3 | -n-C$_3$H$_7$ | -n-C$_3$H$_7$ | —CH$_3$ | —CH$_3$ | 1 | 1 |
| 4 | -n-C$_6$H$_{13}$ | -n-C$_6$H$_{13}$ | —CH$_3$ | —CH$_3$ | 1 | 1 |
| 5 | —CH$_3$ | —CH$_3$ | —O—CH$_3$ | —O—CH$_3$ | 2 | 2 |
| 6 | -n-C$_6$H$_{13}$ | -n-C$_6$H$_{13}$ | —O—CH$_3$ | —O—CH$_3$ | 1 | 1 |
| 7 | —CH$_3$ | —CH$_3$ | -n-C$_3$H$_7$ | -n-C$_3$H$_7$ | 1 | 1 |
| 8 | -n-C$_3$H$_7$ | -n-C$_3$H$_7$ | -n-C$_3$H$_7$ | -n-C$_3$H$_7$ | 1 | 1 |
| 9 | —CH$_3$ | —CH$_3$ | —O-n-C$_3$H$_7$ | —O-n-C$_3$H$_7$ | 1 | 1 |
| 10 | —CH$_3$ | —CH$_3$ | -n-C$_3$H$_7$ | -n-C$_3$H$_7$ | 2 | 2 |
| 11 | —CH$_3$ | —CH$_3$ | —O-n-C$_3$H$_7$ | —O-n-C$_3$H$_7$ | 2 | 2 |
| 12 | -n-C$_3$H$_7$ | -n-C$_3$H$_7$ | —O-n-C$_3$H$_7$ | —O-n-C$_3$H$_7$ | 1 | 1 |
| 13 | -n-C$_3$H$_7$ | -n-C$_3$H$_7$ | —O-n-C$_3$H$_7$ | —O-n-C$_3$H$_7$ | 2 | 2 |
| 14 | -n-C$_6$H$_{13}$ | -n-C$_6$H$_{13}$ | -n-C$_3$H$_7$ | -n-C$_3$H$_7$ | 1 | 1 |
| 15 | -n-C$_6$H$_{13}$ | -n-C$_6$H$_{13}$ | -n-C$_3$H$_7$ | -n-C$_3$H$_7$ | 2 | 2 |
| 16 | -n-C$_6$H$_{13}$ | -n-C$_6$H$_{13}$ | —O-n-C$_3$H$_7$ | —O-n-C$_3$H$_7$ | 2 | 2 |
| 17 | —CH$_3$ | —CH$_3$ | -n-C$_6$H$_{13}$ | -n-C$_6$H$_{13}$ | 1 | 1 |
| 18 | —CH$_3$ | —CH$_3$ | —O-n-C$_6$H$_{13}$ | —O-n-C$_8$H$_{13}$ | 1 | 1 |
| 19 | —CH$_3$ | —CH$_3$ | -n-C$_6$H$_{13}$ | -n-C$_6$H$_{13}$ | 2 | 2 |
| 20 | —CH$_3$ | —CH$_3$ | -n-C$_8$H$_{17}$ | -n-C$_8$H$_{17}$ | 1 | 1 |
| 21 | -n-C$_3$H$_7$ | -n-C$_3$H$_7$ | -n-C$_8$H$_{17}$ | -n-C$_8$H$_{17}$ | 2 | 2 |
| 22 | -n-C$_6$H$_{13}$ | -n-C$_6$H$_{13}$ | -n-C$_8$H$_{13}$ | -n-C$_6$H$_{13}$ | 1 | 1 |
| 23 | -n-C$_6$H$_{13}$ | -n-C$_6$H$_{13}$ | —O-n-C$_6$H$_{13}$ | —O-n-C$_6$H$_{13}$ | 1 | 1 |
| 24 | -n-C$_6$H$_{13}$ | -n-C$_6$H$_{13}$ | -n-C$_8$H$_{17}$ | -n-C$_8$H$_{17}$ | 1 | 1 |
| 25 | -n-C$_6$H$_{13}$ | -n-C$_6$H$_{13}$ | —O-n-C$_8$H$_{17}$ | —O-n-C$_8$H$_{17}$ | 1 | 1 |
| 26 | -n-C$_6$H$_{13}$ | -n-C$_6$H$_{13}$ | -n-C$_8$H$_{17}$ | -n-C$_8$H$_{17}$ | 2 | 2 |
| 27 | -n-C$_6$H$_{13}$ | -n-C$_6$H$_{13}$ | —O-n-C$_8$H$_{17}$ | —O-n-C$_8$H$_{17}$ | 2 | 2 |
| 28 | -n-C$_3$H$_7$ | -n-C$_3$H$_7$ | —O-n-C$_6$H$_{13}$ | —O-n-C$_6$H$_{13}$ | 1 | 2 |
| 29 | -n-C$_6$H$_{13}$ | -n-C$_6$H$_{13}$ | -n-C$_8$H$_{13}$ | -n-C$_8$H$_{17}$ | 1 | 2 |

Hereinafter, the manufacturing method of the fluorene compound of the exemplary embodiment of the invention will be described.

The fluorene compound of the exemplary embodiment can be obtained by utilizing a cross-coupling biaryl synthesis, for example. For example, as the cross-coupling biaryl synthesis, Suzuki reaction, Kharasch reaction, Negishi reaction, Stille reaction, Grignard reaction or Ullmann reaction may be used. More specifically, for example, the fluorene compound of the present exemplary embodiment can be synthesized in accordance with the following scheme, but is not limited thereto. Here, the following scheme shows the manufacturing method of a symmetric compound (referred to as Formula I-1) in which $R_{11}$ and $R_{12}$, $R_{21}$ and $R_{22}$, and n1 and n2 are the same, respectively, in the fluorene compound represented by Formula (I). Accordingly, in the following Formulae (I-1), (IV) and (V), $R_1$ corresponds to $R_{11}$ and $R_{12}$ in Formula (I), $R_2$ corresponds to $R_{21}$ and $R_{22}$ in Formula (I) and n corresponds to n1 and n2 in Formula (I), respectively.

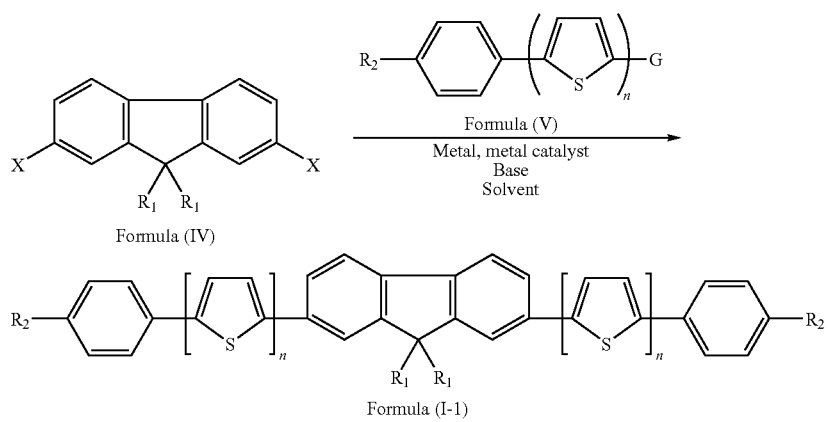

Formula (IV), Formula (V), Formula (I-1)

In Formulae (IV) and (V), X and G each independently represent a halogen atom, $B(OH)_2$, the following Group 1, the following Group 2 or the following Group 3.

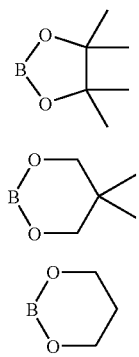

Group 1

Group 2

Group 3

Further, when an asymmetric compound is synthesized, for example, after equimolecular quantities of compounds represented by Formulae (IV-1) and (V-1) are allowed to react with each other to form a compound represented by Formula (I-2), the resultant compound (I-2) is allowed to react with a compound represented by Formula (V-2), whose structure is different from the structure of the compound represented by Formula (V-1) (for example, n1 and n2 are different from each other), but the reaction scheme is not limited thereto. In the following scheme, $R_{11}$ and $R_{12}$, $R_{21}$ and $R_{22}$, and n1 and n2 have the same meanings as those in Formula (I), and X and G have the same meanings as those of Formulae (IV) and (V), respectively.

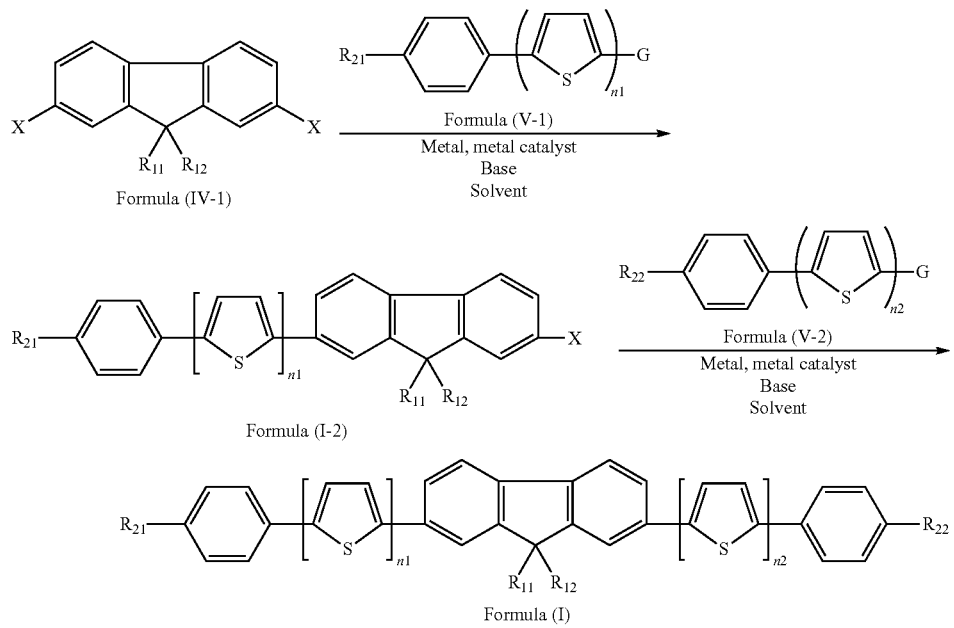

Formula (IV-1), Formula (V-1), Formula (I-2), Formula (V-2), Formula (I)

The metals, metal catalysts and solvents which may be used in the above synthetic reactions, include the followings:

examples of the metal, for example, include Pd, Cu, Ti, Sn, Ni and Pt;

examples of the metal catalyst, for example, include metal complexes (for example, $Pd(PPh_3)_4$, $Pd(OAc)_2$, $Pd_2(dba)_3$, $Pd(PPh_3)_2Cl_2$, $Pd(dppf)_2Cl_2$, Pd/C, $Ni(acac)_2$ and the like), and herein, "dba" represents benzylidene acetone and "dppf" represents bis(diphenylphosphino)ferrocene;

examples of the base, for example, include inorganic bases (for example, $Na_2CO_3$, $K_2CO_3$, $Cs_2CO_3$, $Ba(OH)_2$ and the like), and organic bases (for example, $NEt_3$, $NH(i-Pr)_2$, $NHEt_2$, $NHMe_2$, $NMe_3$, DBU, DMAP, pyridine and the like); and examples of the solvent, which may be any solvent as long as the solvent does not inhibit the reactions, include aromatic hydrocarbon solvents (for example, benzene, toluene, xylene or mesitylene), ether solvents (for example, diethyl ether, tetrahydrofuran or dioxane), acetonitrile, dimethylformamide, dimethyl sulfoxide, methanol, ethanol, isopropyl alcohol, water, $PPh_3$, $P(o-Tol)_3$, $P(t-Bu)_3$ and $PEt_3$.

The above synthetic reactions, for example, may be carried out at ordinary pressure (one atmospheric pressure) under an inert gas atmosphere (for example, nitrogen, argon or the like), but may be carried out under pressurized condition. Further, the reaction temperature in the above synthetic reactions is in the range of from 20° C. to 300° C., and preferably in the range of from 50° C. to 180° C. Moreover, the reaction time of the above synthetic reactions may be selected from the range from several minutes to 20 hours, although the time may vary in accordance with the reaction conditions.

In the above reactions, although the amount the metal or metal complex catalyst to be used is not specifically limited, the amount is from 0.001% by mole to 10% by mole, and is preferably from 0.01% by mole to 5.0% by mole, with respect to the amount of the compound represented by Formula (I).

Further, the amount of the base to be used is in the range of 0.5 to 4.0 by molar ratio, and more preferably, in the range of 1.0 to 2.5 by molar ratio, with respect to the compound represented by Formula (I).

After the completion of the above reaction, the reaction solution is introduced into water, and the mixture is well stirred. When the reaction product is solid (crystal product), a crude product can be obtained by filtering the reaction product off by suction. On the other hand, when the reaction product is an oily product, a crude product can be obtained by extracting the product with a suitable solvent such as ethyl acetate, toluene or the like. Thereafter, the obtained crude product is subjected to column-purification (column-purification using silica gel, alumina, activated clay, active carbon or the like), or alternatively, any of these adsorbents is added to the reaction solution to adsorb unnecessary components to the adsorbents, thereby purifying the crude product. Furthermore, when the reaction product is a crystal, the reaction product is subjected to recrystallization with a suitable solvent (for example, hexane, methanol, acetone, ethanol, ethyl acetate, toluene or the like), thereby purifying the reaction product. In such a manner, the aimed fluorene compound can be obtained.

As described in the above, the fluorene compound according to the exemplary embodiment can be synthesized with ease, and has solubility and film-formability, and charge property (charge transport property and charge injection property). Accordingly, the fluorene compound according to the exemplary embodiment is useful for organic electronic devices such as an electrophotographic photoreceptor, an organic electroluminescent element, an organic transistor, an organic solar cell, an organic optical memory or the like.

EXAMPLES

Hereafter, the invention will be described with reference to examples, but the invention is not limited to the examples.

Example 1

According to the following scheme, in an atmosphere of nitrogen, tetrakis(triphenylphosphine)palladium ($Pd(PPh_3)_4$) (2.3 g) and 2N aqueous sodium carbonate solution (10 ml) are added to a mixed solution of 1-bromo-4-n-octyl benzene (25.0 g), 2-thiopheneboronic acid (10.8 g) and tetrahydrofuran (THF) (100 ml), and the mixture is refluxed for 10 hours. After the reaction is finished, the mixture is subjected to extraction with toluene, and the resultant organic phase is sufficiently washed with pure water. Subsequently, after the organic phase is dried with anhydrous sodium sulfate, the solvent is distilled away under reduced pressure, and the resultant product is subjected to a silica gel column chromatographic process (eluent: hexane) to separate the aimed product, thereby obtaining 26.2 g of Intermediate 1.

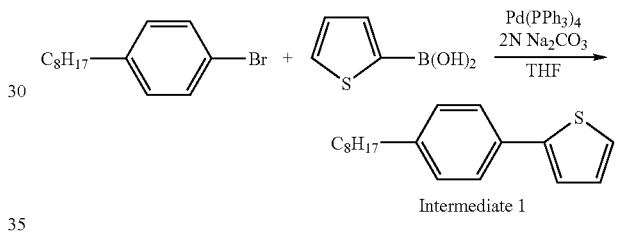

Intermediate 1

Next, according to the following scheme, Intermediate 1 (26.2 g) is dissolved in N,N-dimethylformamide (DMF) (100 ml), and N-bromosuccinimide (NBS) (17.5 g) is added thereto, and the mixture is stirred for 18 hours. After the reaction is finished, the mixture is subjected to extraction with toluene, and the resultant organic phase is sufficiently washed with pure water. Subsequently, after the organic phase is dried with anhydrous sodium sulfate, the solvent is distilled away under reduced pressure, and thus, 28.8 g of Intermediate 2 is obtained.

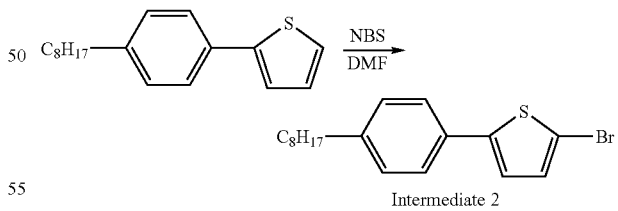

Intermediate 2

Next, according to the following scheme, tetrakis(triphenylphosphine)palladium (2.3 g) and 2N aqueous sodium carbonate solution (5 ml) are added to a mixed solution of Intermediate 2 (5.49 g), 9,9-dihexylfluorene-2,7-diboronic acid (3.0 g) and tetrahydrofuran (100 ml), and the mixture is refluxed for 8 hours. After the reaction is finished, the mixture is subjected to extraction with toluene, and the resultant organic phase is sufficiently washed with pure water. Subsequently, after the organic phase is dried with anhydrous sodium sulfate, the solvent is distilled away under reduced pressure, and the resultant product is subjected to a silica gel column chromatographic process (eluent: hexane) to separate the aimed product, thereby obtaining 2.5 g of Exemplified Compound 24.

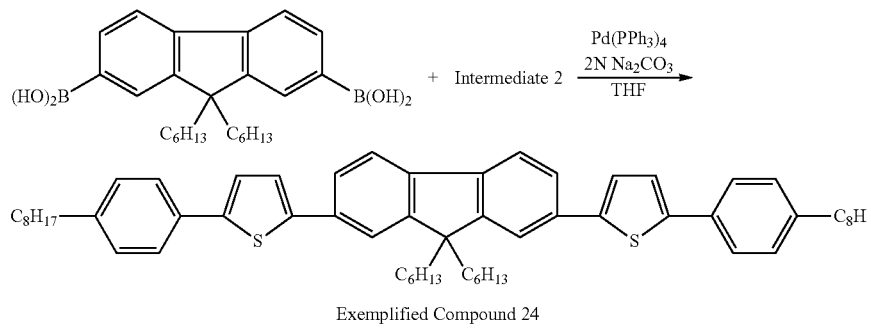

Exemplified Compound 24

The melting point of Exemplified Compound 24 is from 78° C. to 80° C. Exemplified Compound 24 is identified by $^1$H-NMR spectroscopic method ($^1$H-NMR, solvent: CDCl$_3$, UNITY-300 (trade name) manufactured by Varian, Inc., 300 MHz), and IR spectroscopic method (Fourier-transform Infrared Spectrophotometer FT-730 (trade name) manufactured by Horiba, Ltd. (resolution: 4 cm$^{-1}$)) with the use of the KBr method.

Here, details of the infrared absorption spectrum (KBr tablet method) are as follows:

IR(cm$^{-1}$); 792, 863, 1072, 1400, 1444, 1469, 1592, 2854 and 2921.

Details of the $^1$H-NMR (CDCl$_3$) are as follows:

NMR($^1$H, CDCl$_3$): 0.59-1.79 (52H), 1.95-2.16 (4H), 2.59-2.78 (4H), 7.10-7.38 (8H) and 7.45-7.78 (10H).

Example 2

Intermediate 2 (15.0 g) is obtained in a manner similar to Example 1. Next, according to the following scheme, in an atmosphere of nitrogen, tetrakis(triphenylphosphine)palladium (0.9 g) and 2N aqueous sodium carbonate solution (7 ml) are added to a mixed solution of Intermediate 2 (15.0 g), 2-thiopheneboronic acid (6.0 g) and tetrahydrofuran (100 ml), and the mixture is refluxed for 30 hours. After the reaction is finished, the mixture is subjected to extraction with toluene, and the resultant organic phase is sufficiently washed with pure water. Subsequently, after the organic phase is dried with anhydrous sodium sulfate, the solvent is distilled away under reduced pressure, and the resultant product is subjected to a silica gel column chromatographic process (eluent: hexane) to separate the aimed product, thereby obtaining 7.8 g of Intermediate 3.

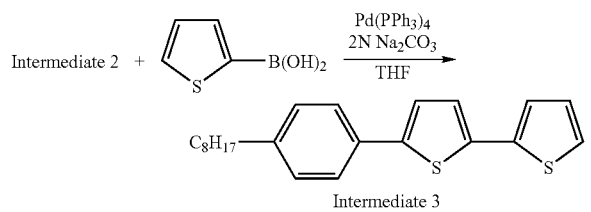

Intermediate 3

Next, according to the following scheme, the intermediate 3 (7.8 g) is dissolved in N,N-dimethylformamide (100 ml), and N-bromosuccinimide (4.1 g) is added thereto, and the mixture is stirred for 18 hours. After the reaction is finished, the mixture is subjected to extraction with toluene, and the resultant organic phase is sufficiently washed with pure water. Subsequently, after the organic phase is dried with anhydrous sodium sulfate, the solvent is distilled away under reduced pressure, and 9.2 g of Intermediate 4 is obtained.

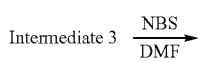

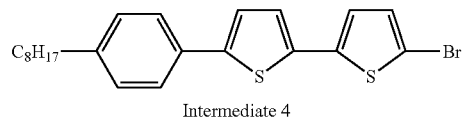

Intermediate 4

Next, according to the following scheme, tetrakis(triphenylphosphine)palladium (0.6 g) and 2N aqueous sodium carbonate solution (7 ml) are added to a mixed solution of the intermediate 4 (9.2 g), 9,9-dihexylfluorene-2,7-diboronic acid (4.2 g) and tetrahydrofuran (100 ml), and the mixture is refluxed for 20 hours. After the reaction is finished, the mixture is subjected to extraction with toluene, and the resultant organic phase is sufficiently washed with pure water. Subsequently, after the organic phase is dried with anhydrous sodium sulfate, the solvent is distilled away under reduced pressure, and the resultant product is subjected to a silica gel column chromatographic process (eluent: hexane) to separate the aimed product, thereby obtaining 1.5 g of Exemplified Compound 26.

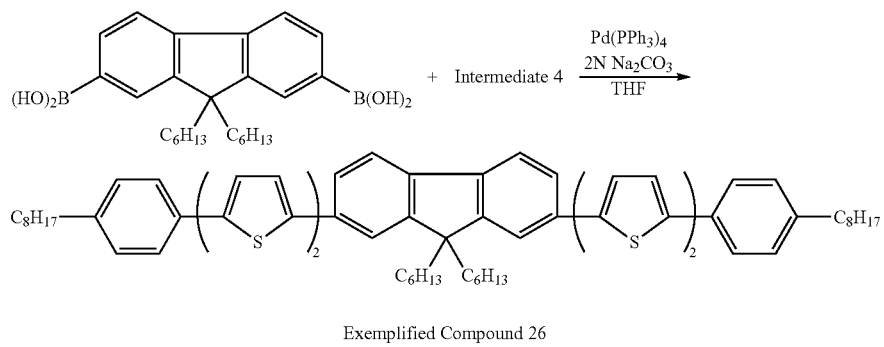

Exemplified Compound 26

The melting point of Exemplified Compound 26 is from 117° C. to 118° C. Exemplified Compound 26 is identified by $^1$H-NMR spectroscopic method and IR spectroscopic method in a manner similar to Example 1.

Figure 2:
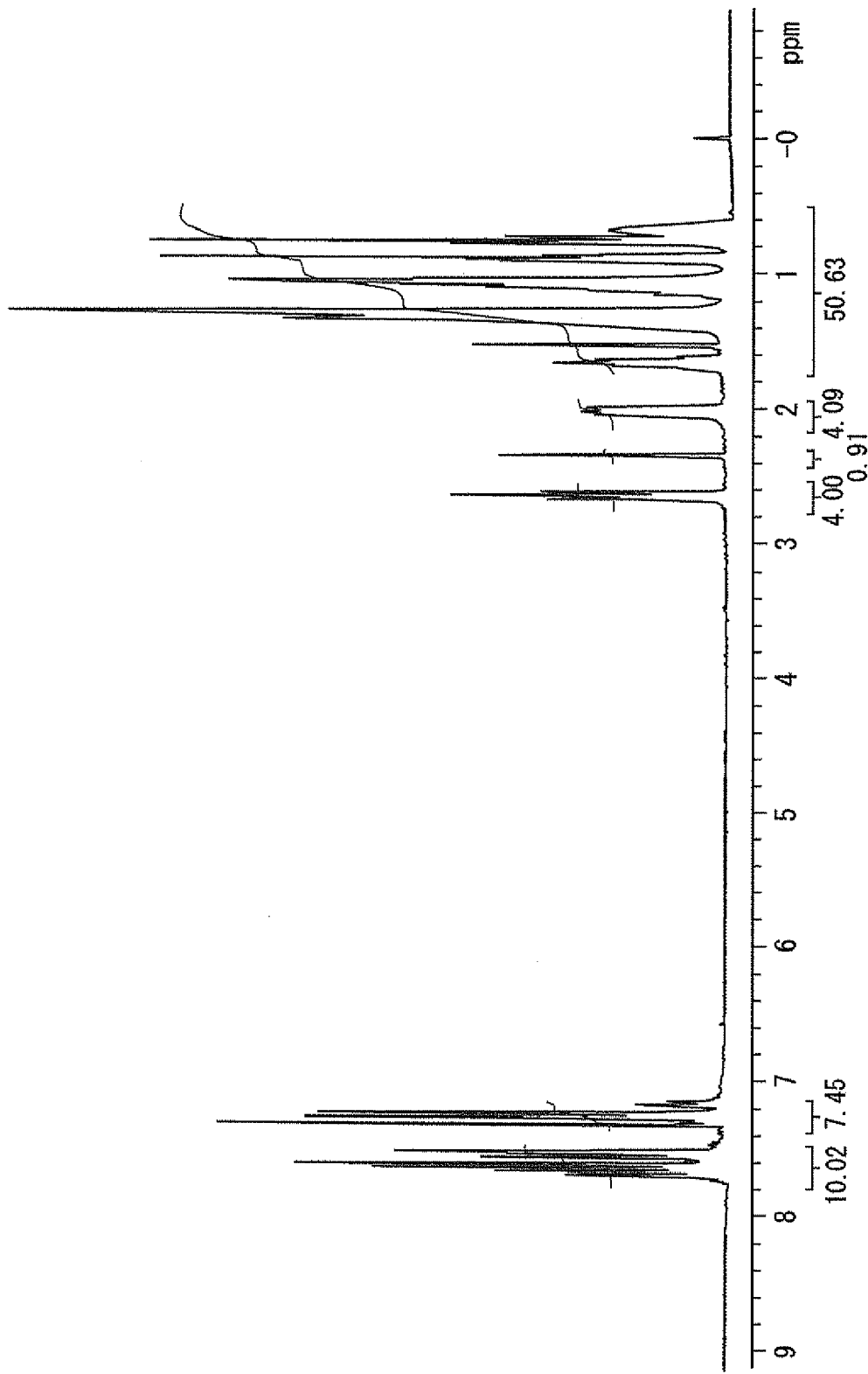
FIG. 2 is a graph showing the NMR spectrum of the compound obtained in Example 2.

The infrared absorption spectrum is shown in FIG. 1, and the NMR spectrum ($^1$H-NMR; solvent: CDCl$_3$, (these conditions are also applied to the description of the following NMR spectrum)) is shown in FIG. 2.

Here, details of the infrared absorption spectrum (KBr tablet method) are as follows:

IR(cm$^{-1}$); 792, 863, 1072, 1400, 1444, 1469, 1592, 2854 and 2921.

Details of the $^1$H-NMR (CDCl$_3$) are as follows:

NMR($^1$H, CDCl$_3$); 0.59-1.45 (52H), 1.89-2.08 (4H), 2.56-2.78 (4H), 7.10-7.38 (11H) and 7.45-7.78 (11H).

Example 3

According to the following scheme, in an atmosphere of nitrogen, a mixed solution obtained by dissolving 1-bromooctane (C$_8$H$_{18}$Br) (30.7 g) in methyl ethyl ketone (15 ml) is added by dropping to a solution obtained by dissolving 4-bromophenol (25.0 g), potassium carbonate (K$_2$CO$_3$) (21.7 g) and tetrabutyl ammonium bromide (TBAB) (2.3 g) in methyl ethyl ketone (MEK) (100 ml). After the mixture is stirred for 5 hours, the resultant organic phase is sufficiently washed with pure water Subsequently, after the organic phase is dried with anhydrous sodium sulfate, the solvent is distilled away under reduced pressure, and the resultant product is subjected to a silica gel column chromatographic process (eluent: hexane) to separate the aimed product, thereby obtaining 42.5 g of Intermediate 5.

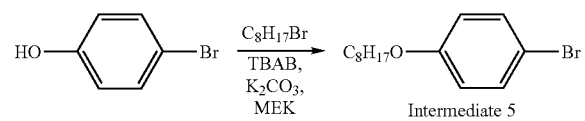

Next, according to the following scheme, in an atmosphere of nitrogen, tetrakis(triphenylphosphine)palladium (1.2 g) and 2N aqueous sodium carbonate solution (7 ml) are added to a mixed solution of the intermediate 5 (15.0 g), 2-thiopheneboronic acid (7.3 g) and tetrahydrofuran (100 ml), and the mixture is refluxed for 8 hours. After the reaction is finished, the mixture is subjected to extraction with toluene, and the resultant organic phase is sufficiently washed with pure water. Subsequently, after the organic phase is dried with anhydrous sodium sulfate, the solvent is distilled away under reduced pressure, and the resultant product is subjected to a silica gel column chromatographic process (eluent: hexane) to separate the aimed product, thereby obtaining 9.1 g of Intermediate 6.

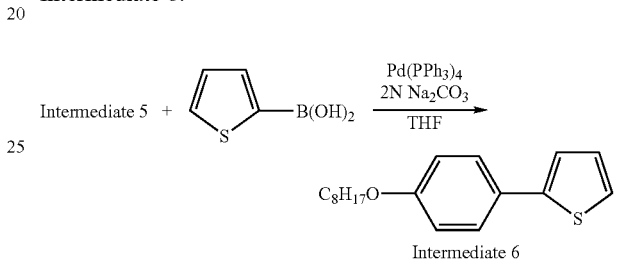

Intermediate 6

Next, according to the following scheme, the intermediate 6 (9.1 g) is dissolved in N,N-dimethylformamide (150 ml), and N-bromosuccinimide (6.1 g) is added thereto, and the mixture is stirred for 18 hours. After the reaction is finished, the mixture is subjected to extraction with toluene, and the resultant organic phase is sufficiently washed with pure water. Subsequently, after the organic phase is dried with anhydrous sodium sulfate, the solvent is distilled away under reduced pressure, thereby obtaining 8.1 g of Intermediate 7.

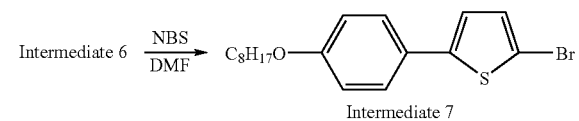

Intermediate 7

Next, according to the following scheme, tetrakis(triphenylphosphine)palladium (1.2 g) and 2N aqueous sodium carbonate solution (5 ml) are added to a mixed solution of the intermediate 7 (5.7 g), 9,9-dihexylfluorene-2,7-diboronic acid (3.0 g) and tetrahydrofuran (100 ml), and the mixture is refluxed for 8 hours. After the reaction is finished, the mixture is extracted with toluene, and the resultant organic phase is sufficiently washed with pure water. Subsequently, after the organic phase is dried with anhydrous sodium sulfate, the solvent is distilled away under reduced pressure, the resultant product is subjected to a silica gel column chromatographic process (eluent:hexane:toluene=3:1) to separate the aimed product, and the separated product is recrystallized with isopropyl alcohol, thereby obtaining 2.7 g of Exemplified Compound 25.

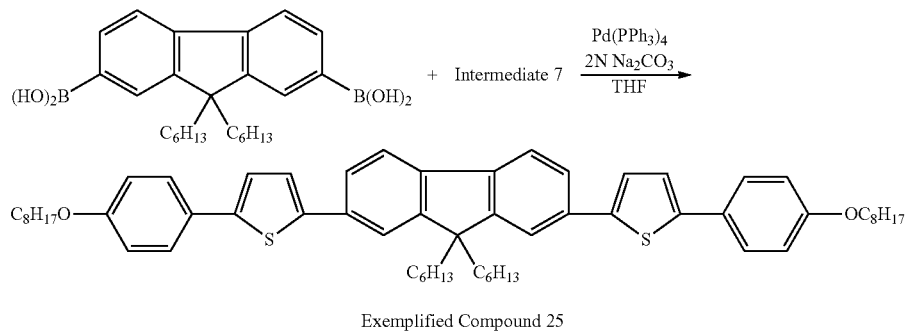

Exemplified Compound 25

The melting point of Exemplified Compound 25 is from 96° C. to 97° C. Exemplified Compound 25 is identified by $^1$H-NMR spectroscopic method and IR spectroscopic method in a manner similar to Example 1.

Here, details of the infrared absorption spectrum (KBr tablet method) are as follows:

IR(cm$^{-1}$); 798, 833, 1465, 2850 and 2952.

Details of the $^1$H-NMR (CDCl$_3$) are as follows:

NMR($^1$H, CDCl$_3$); 0.59-1.55 (48H), 1.62-1.78 (4H), 1.91-2.08 (4H), 3.85-3.98 (4H), 6.79-6.92 (4H), 7.14 (2H), 7.26 (2H) and 7.42-7.76 (10H).

Example 4

Intermediate 7 (10.0 g) is obtained in a manner similar to Example 3. Next, according to the following scheme, in an atmosphere of nitrogen, tetrakis(triphenylphosphine)palladium (0.6 g) and 2N aqueous sodium carbonate solution (7 ml) are added to a mixed solution of Intermediate 7 (10.0 g), 2-thiopheneboronic acid (3.8 g) and tetrahydrofuran (100 ml), and the mixture is refluxed for 50 hours. After the reaction is finished, the mixture is subjected to extraction with toluene, and the resultant organic phase is sufficiently washed with pure water. Subsequently, after the organic phase is dried with anhydrous sodium sulfate, the solvent is distilled away under reduced pressure, and the resultant product is subjected to a silica gel column chromatographic process (eluent: toluene) to separate the aimed product, thereby obtaining 7.9 g of Intermediate 8.

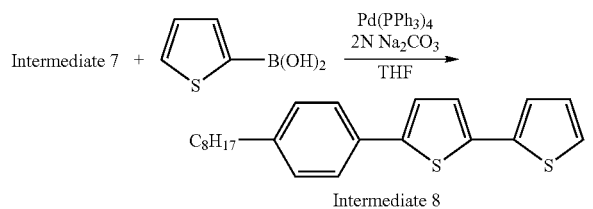

Intermediate 8

Next, according to the following scheme, Intermediate 8 (7.9 g) is dissolved in N,N-dimethylformamide (300 ml), and N-bromosuccinimide (3.4 g) is added thereto, and the mixture is stirred for 18 hours. After the reaction is finished, the mixture is subjected to extraction with toluene, and the resultant organic phase is sufficiently washed with pure water. Subsequently, after the organic phase is dried with anhydrous sodium sulfate, the solvent is distilled away under reduced pressure, and thus, 5.6 g of Intermediate 9 is obtained.

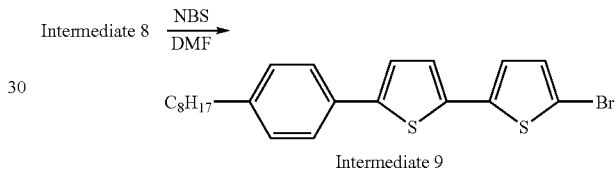

Intermediate 9

Next, according to the following scheme, tetrakis(triphenylphosphine)palladium (1.2 g) and 2N aqueous sodium carbonate solution (5 ml) are added to a mixed solution of Intermediate 9 (5.6 g), 9,9-dihexylfluorene-2,7-diboronic acid (3.0 g) and tetrahydrofuran (100 ml), and the mixture is refluxed for 12 hours. After the reaction is finished, the mixture is subjected to extraction with toluene, and the resultant organic phase is sufficiently washed with pure water. Subsequently, after the organic phase is dried with anhydrous sodium sulfate, the solvent is distilled away under reduced pressure, the resultant product is subjected to a silica gel column chromatographic process (eluent: toluene) to separate the aimed product, and the separated product is recrystallized with a mixed solvent of isopropyl alcohol and toluene, thereby obtaining 3.4 g of Exemplified Compound 27.

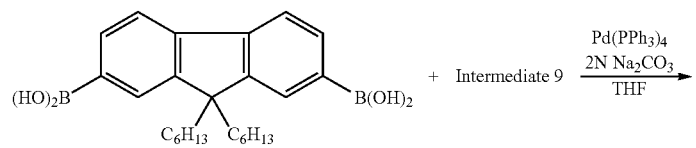

-continued

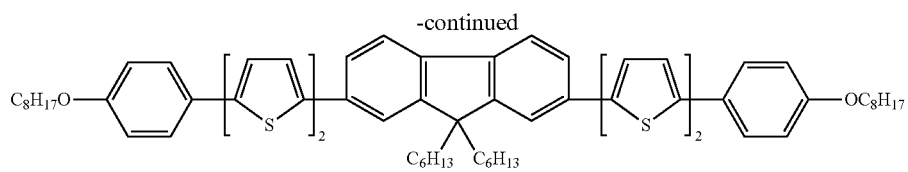

Exemplified Compound 27

The melting point of Exemplified Compound 27 is from 140° C. to 141° C. Exemplified Compound 27 is identified by the $^1$H-NMR spectroscopic method and the IR spectroscopic method in a manner similar to Example 1.

Here, details of the infrared absorption spectrum (KBr tablet method) are as follows:

IR(cm$^{-1}$); 609, 809, 1334, 1421, 2850 and 2954.

Details of the $^1$H-NMR (CDCl$_3$) are as follows:

NMR($^1$H, CDCl$_3$); 0.59-1.58 (48H), 1.72-1.85 (4H), 1.91-2.10 (4H), 3.85-4.01 (4H), 6.81-6.98 (4H), 7.14-7.20 (6H), 7.21-7.38 (2H) and 7.42-7.76 (10H).

Evaluation

Films are formed in the manner described below with the use of the exemplified compounds obtained in the above examples, and the charge mobility is measured.

After one part by weight of the respective Exemplified Compound and 4 parts by weight of a bisphenol (Z) polymer compound (viscosity average molecular weight: 40,000) represented by the following Compound A are dissolved in 50 parts by weight of chlorobenzene, a film is formed using a doctor blade, and dried with a hot plate.

The charge mobility is measured in accordance with the Time of Flight (TOF) method using a TOF-401 ((trade name) manufactured by Optel Ltd. (excitation light source: nitrogen pulse laser (wavelength: 337 nm); applied voltage: 30 V/μm)). The results are shown in Table 1.

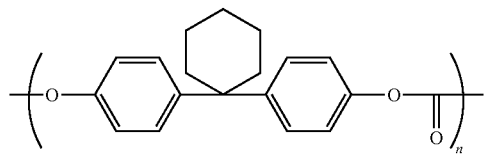

Compound A

TABLE 1

| | Charge Mobility (cm$^2$/Vs) |
|---|---|
| Example 1 | 4.1 × 10$^{-7}$ |
| Example 2 | 8.6 × 10$^{-8}$ |
| Example 3 | 7.9 × 10$^{-8}$ |
| Example 4 | Photocurrent waveform is observed, but cannot be quantified. |

As can be seen from the above results, the exemplified compounds obtained in Examples are fluorene compounds having solubility and film-formability, and charge property (charge transport property and charge injection property), and are useful for various organic electronic devices. Further, the exemplified compounds obtained in Examples can be synthesized with ease.

What is claimed is:

1. A fluorene compound represented by the following Formula (I):

Formula (I)

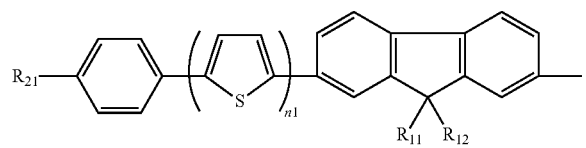

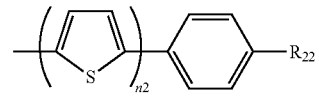

wherein, in Formula (I), $R_{11}$ and $R_{12}$ each independently represent an alkyl group having 1 to 6 carbon atoms; $R_{21}$ represents an alkyl group having 1 to 8 carbon atoms, or an alkoxy group having 1 to 8 carbon atoms; n1 and n2 each independently represent an integer of from 1 to 5; and $R_{22}$ is an alkyl group having 3 to 6 carbon atoms.

2. A fluorene compound represented by the following Formula (I):

Formula (I)

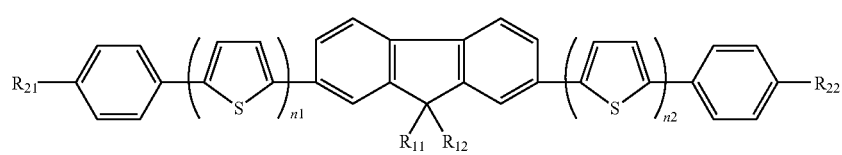

wherein, in Formula (I), $R_{11}$ and $R_{12}$ each independently represent an alkyl group having 1 to 6 carbon atoms; $R_{21}$ and $R_{22}$ each independently represent an alkyl group having 1 to 8 carbon atoms, or an alkoxy group having 1 to 8 carbon atoms; and n1 and n2 each independently represent an integer of from 2 to 5.

3. The fluorene compound according to claim 2, wherein $R_{11}$ is an alkyl group having 3 to 6 carbon atoms.

4. The fluorene compound according to claim 2, wherein $R_{12}$ is an alkyl group having 3 to 6 carbon atoms.

5. The fluorene compound according to claim 2, wherein $R_{11}$ is a methyl group, an ethyl group, an n-propyl group, an isopropyl group, an n-butyl group, a t-butyl group, a pentyl group or a hexyl group.

6. The fluorene compound according to claim 2, wherein $R_{12}$ is a methyl group, an ethyl group, an n-propyl group, an isopropyl group, an n-butyl group, a t-butyl group, a pentyl group or a hexyl group.

7. The fluorene compound according to claim 2, wherein the alkyl group represented by $R_{11}$ is straight-chained or branch-chained.

8. The fluorene compound according to claim 2, wherein the alkyl group represented by $R_{12}$ is straight-chained or branch-chained.

9. The fluorene compound according to claim 2, wherein $R_{21}$ is an alkyl group having 3 to 6 carbon atoms.

10. The fluorene compound according to claim 2, wherein $R_{21}$ is a methyl group, an ethyl group, an n-propyl group, an isopropyl group, an n-butyl group, a t-butyl group, a pentyl group, a hexyl group, a heptyl group or an octyl group.

11. A fluorene compound represented by the following Formula (I):

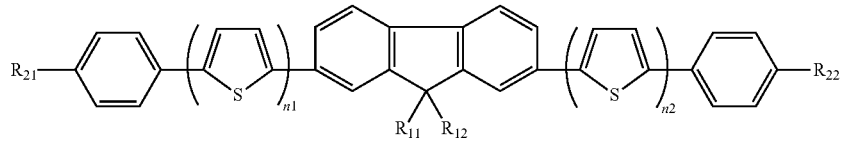

Formula (I)

wherein, in Formula (I), $R_{11}$ and $R_{12}$ each independently represent an alkyl group having 1 to 6 carbon atoms; $R_{21}$ represents an alkyl group having 1 to 8 carbon atoms, or an alkoxy group having 1 to 8 carbon atoms; n1 and n2 each independently represent an integer of from 1 to 5; and $R_{22}$ is a methyl group, an ethyl group, an n-propyl group, an isopropyl group, an n-butyl group, a t-butyl group, a pentyl group, a hexyl group, a heptyl group or an octyl group.

12. The fluorene compound according to claim 2, wherein $R_{21}$ represents an alkyl group, and the alkyl group represented by $R_{21}$ is straight-chained or branch-chained.

13. A fluorene compound represented by the following Formula (I):

wherein, in Formula (I), $R_{11}$ and $R_{12}$ each independently represent an alkyl group having 1 to 6 carbon atoms; $R_{21}$ represents an alkyl group having 1 to 8 carbon atoms, or an alkoxy group having 1 to 8 carbon atoms; n1 and n2 each independently represent an integer of from 1 to 5; and $R_{22}$ represents an alkyl group, and the alkyl group represented by $R_{22}$ is straight-chained or branch-chained.

14. The fluorene compound according to claim 2, wherein $R_{21}$ is an alkoxy group having 3 to 6 carbon atoms.

15. The fluorene compound according to claim 2, wherein $R_{21}$ is a methoxy group, an ethoxy group, an n-propoxy group, an isopropoxy group, an n-butoxy group, a t-butoxy group or a pentyloxy group.

16. The fluorene compound according to claim 2, wherein $R_{21}$ represents an alkoxy group, and the alkoxy group represented by $R_{21}$ is straight-chained or branch-chained.

17. The fluorene compound according to claim 2, wherein n1 and n2 each independently represent an integer of 1 to 3.

18. The fluorene compound according to claim 2, wherein the fluorene compound is a symmetric compound.

19. The fluorene compound according to claim 2, wherein $R_{22}$ is an alkoxy group having 3 to 6 carbon atoms.

20. The fluorene compound according to claim 2, wherein $R_{22}$ is a methoxy group, an ethoxy group, an n-propoxy group, an isopropoxy group, an n-butoxy group, a t-butoxy group or a pentyloxy group.

* * * * *